US009844496B2

(12) United States Patent
Jung et al.

(10) Patent No.: US 9,844,496 B2
(45) Date of Patent: Dec. 19, 2017

(54) FOAM HAVING IMPROVED FEELING DURING USE

(71) Applicant: AMOREPACIFIC CORPORATION, Seoul (KR)

(72) Inventors: Ha Jin Jung, Yongin-si (KR); Kyung Nam Kim, Yongin-si (KR); Jung Sun Choi, Yongin-si (KR); Kyung Ho Choi, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 37 days.

(21) Appl. No.: 14/391,088

(22) PCT Filed: Apr. 12, 2013

(86) PCT No.: PCT/KR2013/003101
§ 371 (c)(1),
(2) Date: Oct. 7, 2014

(87) PCT Pub. No.: WO2013/154392
PCT Pub. Date: Oct. 17, 2013

(65) Prior Publication Data
US 2015/0117931 A1 Apr. 30, 2015

(30) Foreign Application Priority Data

Apr. 12, 2012 (KR) .................. 10-2012-0038132
Apr. 11, 2013 (KR) .................. 10-2013-0039638

(51) Int. Cl.
| | |
|---|---|
| C08J 9/40 | (2006.01) |
| A45D 34/00 | (2006.01) |
| A61Q 19/00 | (2006.01) |
| A61K 8/02 | (2006.01) |
| A61K 8/04 | (2006.01) |
| A45D 34/04 | (2006.01) |
| A45D 40/26 | (2006.01) |
| A61Q 17/04 | (2006.01) |
| A61K 8/81 | (2006.01) |
| A61K 8/85 | (2006.01) |
| A61K 8/86 | (2006.01) |

(52) U.S. Cl.
CPC ............ *A61K 8/0208* (2013.01); *A45D 34/00* (2013.01); *A45D 34/04* (2013.01); *A45D 40/26* (2013.01); *A61K 8/046* (2013.01); *A61K 8/8123* (2013.01); *A61K 8/8194* (2013.01); *A61K 8/85* (2013.01); *A61K 8/86* (2013.01); *A61Q 17/04* (2013.01); *A61Q 19/00* (2013.01); *C08J 9/40* (2013.01); *A45D* *2200/1018* (2013.01); *A45D 2200/1036* (2013.01); *A61K 2800/87* (2013.01); *C08J 2201/036* (2013.01); *C08J 2307/00* (2013.01); *C08J 2309/02* (2013.01); *C08J 2309/06* (2013.01); *C08J 2323/06* (2013.01); *C08J 2327/06* (2013.01); *C08J 2331/04* (2013.01); *C08J 2371/00* (2013.01)

(58) Field of Classification Search
CPC combination set(s) only.
See application file for complete search history.

(56) References Cited

U.S. PATENT DOCUMENTS

| | | | |
|---|---|---|---|
| 5,762,946 A | 6/1998 | Gueret | |
| 7,811,021 B2* | 10/2010 | Gueret | .................. A45D 33/02 401/196 |
| 8,367,083 B2* | 2/2013 | Barba | .................... A61K 8/891 424/401 |
| 2007/0277844 A1 | 12/2007 | Gueret | |
| 2009/0197948 A1* | 8/2009 | Miyahara | ................ A61K 8/90 514/474 |
| 2011/0014254 A1 | 1/2011 | Choi et al. | |

FOREIGN PATENT DOCUMENTS

| | | |
|---|---|---|
| EP | 0528705 | 2/1993 |
| EP | 2425961 A1 | 3/2012 |
| JP | S5755409 | 9/1955 |
| JP | S6272732 A | 4/1987 |
| JP | 3015878 U | 9/1995 |
| JP | 07095964 B2 | 10/1995 |
| JP | H09220118 A | 8/1997 |
| JP | 2002255736 A | 9/2002 |
| JP | 2003012457 A | 1/2003 |
| JP | 2007508086 A | 4/2007 |
| JP | 2009019008 A | 1/2009 |
| JP | 2011132154 | 7/2011 |
| KR | 1020000013194 A | 3/2000 |
| KR | 1020090100643 A | 9/2009 |
| KR | 1020100101278 A | 9/2010 |
| KR | 1020100128163 A | 12/2010 |
| WO | 2005039350 A1 | 6/2005 |

OTHER PUBLICATIONS

International Search Report for International Application No. PCT/KR2013/003101 dated Jul. 3, 2013.
Japan Office Action in Corresponding Patent Application No. JP 2015505648 dated Mar. 10, 2017, with Partial English Translation.

* cited by examiner

*Primary Examiner* — David Walczak
(74) *Attorney, Agent, or Firm* — Cantor Colburn LLP

(57) ABSTRACT

The present invention relates to a foam made of a specific material having superior properties and to cosmetics comprising said foam.

11 Claims, 1 Drawing Sheet

|  | Comp. Ex. | Ex.1 | Ex.2 | Ex.3 | Ex.4 | Ex.5 |
|---|---|---|---|---|---|---|
| Images |  | 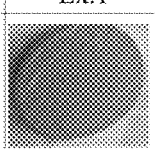 | 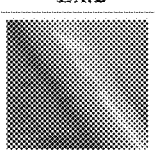 | 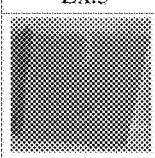 | 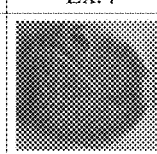 | 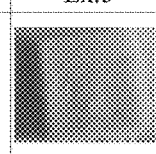 |
| Adhesion | 1 | 5 | 4 | 4 | 4 | 5 |
| Finish | 1 | 4 | 4 | 4 | 4 | 4 |
| Thin application | 2 | 5 | 4 | 4 | 4 | 5 |
| Soft applicability | 1 | 4 | 4 | 4 | 5 | 4 |
| Consistency | 1 | 4 | 4 | 4 | 4 | 5 |
| Uniformness | 1 | 4 | 4 | 4 | 4 | 5 |
| Softness | 1 | 4 | 4 | 4 | 5 | 4 |
| Smoothness | 2 | 4 | 5 | 4 | 4 | 5 |
| Improved skin texture | 1 | 4 | 4 | 5 | 4 | 4 |
| Silkiness | 2 | 4 | 4 | 5 | 4 | 4 |

FOAM HAVING IMPROVED FEELING DURING USE

TECHNICAL FIELD

The present disclosure relates to a foam having superior properties and a cosmetic comprising the same.

BACKGROUND ART

A cosmetic composition is commonly provided as stored in a vacuum container, a pump container or a glass container. However, these containers are inconvenient to carry. Recently, as the necessity of putting on or adjusting makeup outdoors increases, there is a need of a cosmetic composition that can be carried conveniently.

A compact-type container may be considered as a container capable of conveniently carrying a cosmetic composition. In order to hold a liquid cosmetic composition in the compact-type container, it should be considered whether the container is compatible with the carrier for cosmetic composition, whether the cosmetic composition can be effectively held in the carrier, whether the carrier can hold the cosmetic composition stably for a long time and whether an adequate amount of the cosmetic composition can be ejected from the carrier.

The inventors of the present disclosure have found out that a foam prepared from a specific material provides superior skin adhesion, finish, thin application, soft applicability, consistency, uniformness, softness, smoothness, improved skin texture or silkiness.

More specifically, the inventors of the present disclosure have confirmed that a foam prepared from a specific material provides superior skin adhesion, reduced skin roughness, improved skin texture or improved applicability.

BRIEF DESCRIPTION OF THE DRAWINGS

The FIGURE is a table showing the results of a panel evaluation on a scale of 1 (very poor) to 5 (very good) of several parameters relating to hand application of a cosmetic composition after storage each of the foams of Examples 1 to 5 compared to direct hand application of the cosmetic composition (Comp. Ex) and a photographic image of each foam.

DISCLOSURE

Technical Problem

The inventors of the present disclosure have found out that when an adequate amount of a cosmetic composition absorbed in a specific foam is taken with a hand and applied on the face, feeling of use is remarkably improved over when the cosmetic composition not absorbed in the foam is directly applied on the face. The present disclosure is directed to providing a foam providing improved feeling of use and a cosmetic comprising the same.

Technical Solution

In one general aspect, the present disclosure provides a foam for improving skin adhesion of a cosmetic composition, consisting of one or more material selected from a group consisting of acrylonitrile-butadiene rubber (NBR), styrene-butadiene rubber (SBR) and natural rubber (NR), and a cosmetic comprising the same.

In another general aspect, the present disclosure provides a foam for reducing skin roughness of a cosmetic composition, comprising one or more material selected from a group consisting of polyvinyl chloride, polyethylene and ethylene-vinyl acetate (EVA), and a cosmetic comprising the same.

In another general aspect, the present disclosure provides a foam for improving skin texture of a cosmetic composition, comprising one or more material selected from a group consisting of latex, silicone, film-type, styrene-isoprene-styrene (SIS), styrene-ethylene-butylene-styrene (SEBS), polyvinyl alcohol (PVA), silicone elastomer, nitrile, butyl, polyether and neoprene, and a cosmetic comprising the same.

Advantageous Effects

Foams of the present disclosure includes various materials so that provide improved skin adhesion, reduced skin roughness, improved skin texture or improved applicability and allow convenient use of a cosmetic composition with improved stability and portability. Since the foams have different uses, they may provide optimized feeling of use of cosmetics.

BEST MODE

As used herein, a "foam" refers to a polymer foamed by dry or wet foaming.

As used herein, "flocking" refers to a process of depositing very short fibers (flock) onto, e.g., a foam.

As used herein, "impregnation" means that a cosmetic composition is carried in a foam.

In an aspect, the present disclosure provides a foam for impregnating a cosmetic composition, comprising one or more material selected from a group consisting of acrylonitrile-butadiene rubber (NBR), styrene-butadiene rubber (SBR), natural rubber (NR), polyvinyl chloride, polyethylene, ethylene-vinyl acetate (EVA), latex, silicone, film-type, styrene-isoprene-styrene (SIS), styrene-ethylene-butylene-styrene (SEBS), polyvinyl alcohol (PVA), silicone elastomer, nitrile, butyl, polyether and neoprene.

In an exemplary embodiment of the present disclosure, the foam may be flocked with cotton, cotton/acryl, cotton/acryl/polyester, cotton/rayon, acryl, polyamide, nylon, polyester, nylon/polyester or silk.

In another aspect, the present disclosure provides a foam for improving skin adhesion of a cosmetic composition, comprising a rubber, for example, one or more material selected from a group consisting of acrylonitrile-butadiene rubber (NBR), styrene-butadiene rubber (SBR) and natural rubber (NR).

"Improved skin adhesion" means that, when a cosmetic composition impregnated in the foam is applied to the skin, the cosmetic composition is tightly adhered to the surface of the skin without getting loose. The foam of the present disclosure is advantageous in that the cosmetic composition can be applied on the skin tightly, thinly and uniformly and thus can provide silkiness to the skin.

In another aspect, the present disclosure provides a cosmetic comprising: the foam; and a cosmetic composition impregnated in the foam.

In another aspect, the present disclosure provides a foam for reducing skin roughness of a cosmetic composition, comprising a vinyl, for example, one or more material selected from a group consisting of polyvinyl chloride, polyethylene and ethylene-vinyl acetate (EVA).

"Reduced skin roughness" means that, when a cosmetic composition impregnated in the foam is applied to the skin, the cosmetic composition makes the skin surface even by filling the unevenness of the skin. The roughness of the skin may be formed by pimples, scars or pores, but is not limited thereto.

In another aspect, the present disclosure provides a cosmetic comprising: the foam; and a cosmetic composition impregnated in the foam.

In another aspect, the present disclosure provides a foam for improving skin texture of a cosmetic composition, comprising a silicone, for example, one or more material selected from a group consisting of latex, silicone, film-type, styrene-isoprene-styrene (SIS), styrene-ethylene-butylene-styrene (SEBS), polyvinyl alcohol (PVA), silicone elastomer, nitrile, butyl, polyether and neoprene.

"Improving skin texture" means, when the skin tone is nonuniform due to intrinsic or extrinsic factors or when the skin texture is bumpy, making the skin tone uniform or making the skin texture smooth. The skin tone may be nonuniform due to pigmentation, aging, exposure to UV, etc., but is not limited thereto.

In another aspect, the present disclosure provides a cosmetic comprising: the foam; and a cosmetic composition impregnated in the foam.

In another aspect, the present disclosure provides a foam for improving skin applicability of a cosmetic composition, wherein the foam described above is flocked with cotton, cotton/acryl, cotton/acryl/polyester, cotton/rayon, acryl, polyamide, nylon, polyester, nylon/polyester or silk.

"Improved skin applicability" means that the cosmetic composition can be applied thinly and uniformly on the skin without scrubbing or coming off and, thus, a natural feeling of use is provided.

In another aspect, the present disclosure provides a cosmetic comprising: one or more of the foam; and a cosmetic composition impregnated in the foam.

In an exemplary embodiment of the present disclosure, the cosmetic composition may be in liquid or solid state. Specifically, the cosmetic composition may be solution, emulsion, gel, cream or suspension.

In an exemplary embodiment of the present disclosure, the cosmetic composition may be an aqueous dispersion, an oily dispersion, a water-in-oil (W/O) emulsion or an oil-in-water (O/W) emulsion.

In general, a cosmetic composition in liquid state is difficult to carry and store as compared to one in solid state. However, the cosmetic comprising the foam according to the present disclosure is advantageous in that even a cosmetic composition in liquid or cream state can be stored and carried stably and safely. If the cosmetic composition is in solid state, it can be comprised in the carrier (foam) to reduce instant change in physical properties due to heat or external impact. Further, since the carrier serves to fix the cosmetic composition, an adequate amount of the content can be ejected.

In an exemplary embodiment of the present disclosure, the cosmetic composition that may be comprised in the cosmetic may be an emulsion composition, specifically a water-in-oil (W/O) emulsion or an oil-in-water (O/W) emulsion, or a dispersion composition, specifically an oily dispersion or an aqueous dispersion.

In an exemplary embodiment of the present disclosure, the cosmetic composition that may be comprised in the cosmetic may be prepared into, for example, makeup primer, makeup base, liquid or solid foundation, concealer, lipstick, lip gloss, powder, lip liner, eyebrow, eye shadow, blusher (blusher), twin cake, sunscreen, lotion, cream, essence, etc., but is not limited thereto.

In an exemplary embodiment of the present disclosure, the cosmetic impregnated in the foam may be applied to the skin using a hand or an applicator (e.g., puff).

Hereinafter, the present disclosure will be described in detail through examples. However, the following examples are for illustrative purposes only and it will be apparent to those of ordinary skill in the art that the scope of the present disclosure is not limited by the examples.

Preparation Example

A cosmetic composition (emulsion) containing the components described in Table 1 was impregnated in foams of Examples 1-5.

TABLE 1

| Components | Contents (wt %) |
|---|---|
| Ozokerite | 0.1 |
| Dicaprylyl carbonate | 10.0 |
| Methylparaben | 0.1 |
| Octyl methoxycinnamate | 7.0 |
| Isoamyl p-methoxycinnamate | 2.0 |
| Disteardimonium hectorite | 0.2 |
| Decamethylcyclopentasiloxane | 16.0 |
| Sorbitan sesquioleate | 2.0 |
| Lauryl PEG/PPG-18/18 methicone | 1.5 |
| Poly(methyl methacrylate) | 5.0 |
| Titanium dioxide/aluminum hydroxide/stearic acid | 7.0 |
| Water | To 100 |
| Glycerine | 8.0 |
| Salt | 1.0 |
| Fragrance | 0.4 |
| Total | 100.0 |

Comparative Example

At room temperature, 0.5 g of the cosmetic composition was taken with a hand and applied onto the face.

Example 1

At room temperature, the cosmetic composition was impregnated in a foam prepared from acrylonitrile-butadiene rubber (NBR) and having a diameter of 48 mm and a thickness of 50 mm. After waiting for 2 hours until stabilization, 0.5 g of the cosmetic composition was ejected from the foam by pressing with a hand and applied onto the face.

Example 2

At room temperature, the cosmetic composition was impregnated in a foam prepared from polyvinyl chloride and having a diameter of 48 mm and a thickness of 50 mm. After waiting for 2 hours until stabilization, 0.5 g of the cosmetic composition was ejected from the foam by pressing with a hand and applied onto the face.

Example 3

At room temperature, the cosmetic composition was impregnated in a foam prepared from latex and having a diameter of 48 mm and a thickness of 50 mm. After waiting for 2 hours until stabilization, 0.5 g of the cosmetic composition was ejected from the foam by pressing with a hand and applied onto the face.

Example 4

At room temperature, the cosmetic composition was impregnated in a foam prepared from polyether and flocked with polyester and having a diameter of 48 mm and a thickness of 50 mm. After waiting for 2 hours until stabilization, 0.5 g of the cosmetic composition was ejected from the foam by pressing with a hand and applied onto the face.

Example 5

At room temperature, the cosmetic composition was impregnated in a foam prepared from polyether and having a diameter of 48 mm and a thickness of 50 mm. After waiting for 2 hours until stabilization, 0.5 g of the cosmetic composition was ejected from the foam by pressing with a hand and applied onto the face.

Test Example

Evaluation was performed by 5 professional women panels who were aged 24-35 years, had makeup experiences for at least 2 years and wore makeup at least 5 times a week. They were asked to evaluate each test item with 5-point standards (1: very poor, 2: poor, 3: moderate, 4: good, 5: very good). The result is given in Table 2.

'Adhesion' is indicative of skin adhesion. 'Finish' is indicative of stickiness or other residual feeling after application to the skin. 'Thin application' is indicative of thickness of makeup after application to the skin. 'Soft applicability' is indicative of applicability to the skin. 'Consistency' is indicative of consistency of makeup after application to the skin. 'Uniformness' is indicative of reduced partial lumping after application. 'Softness' is indicative of baby face-like softness after application. 'Smoothness' is indicative of reduced skin roughness. 'Improved skin texture' is indicative of mending of skin tone or providing of smooth skin texture. 'Silkiness' is indicative of smooth application to the skin.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A cosmetic, comprising
    a carrier foam comprising one or more materials selected from the group consisting of acrylonitrile-butadiene rubber (NBR), polyvinyl chloride, latex, and polyether, and
    impregnated therein a cosmetic composition comprising octyl methoxycinnamate, wherein the carrier foam stores the cosmetic composition.

2. The cosmetic according to claim 1, wherein the foam is flocked with cotton, cotton/acryl, cotton/acryl/polyester, cotton/rayon, acryl, polyamide, nylon, polyester, nylon/polyester or silk.

3. The cosmetic according to claim 1,
    wherein the one or more material is acrylonitrile-butadiene rubber (NBR).

4. The cosmetic according to claim 3, wherein the foam is flocked with cotton, cotton/acryl, cotton/acryl/polyester, cotton/rayon, acryl, polyamide, nylon, polyester, nylon/polyester or silk.

5. The cosmetic of claim 1, wherein the cosmetic composition comprises Ozokerite, Dicaprylyl carbonate, Methylparaben, Isoamyl p-methoxycinnamate, Disteardimonium hectorite, Decamethylcyclopentasiloxane, Sorbitan sesquioleate, Lauryl PEG/PPG-18/18 methicone, Poly(methyl methacrylate), Titanium dioxide/aluminum hydroxide/stearic acid, Water, Glycerine, Salt, and Fragrance.

6. The cosmetic of claim 1, wherein the cosmetic composition further comprises Isoamyl p-methoxycinnamate.

7. The cosmetic of claim 6, further comprising Decamethylcyclopentasiloxane.

8. The cosmetic of claim 7, further comprising Ozokerite, Dicaprylyl carbonate, Methylparaben, Disteardimonium hectorite, Sorbitan sesquioleate, Lauryl PEG/PPG-18/18 methicone, Poly(methyl methacrylate), Titanium dioxide/aluminum hydroxide/stearic acid, Water, Glycerine, Salt, and Fragrance.

9. The cosmetic according to claim 1, wherein the cosmetic composition is in liquid or solid state.

10. The cosmetic according to claim 1, wherein the cosmetic composition is an aqueous dispersion, an oily dispersion, a water-in-oil (W/O) emulsion or an oil-in-water (O/W) emulsion.

11. The cosmetic of claim 1, further comprising an applicator.

* * * * *